United States Patent [19]
Field et al.

[11] Patent Number: 6,048,485
[45] Date of Patent: Apr. 11, 2000

[54] THERMAL GRADIENT BEVELING OF CATHETERS

[75] Inventors: J. Douglas Field, Avon; Roger Ahlstrom, Southington, both of Conn.

[73] Assignee: Johnson & Johnson Medical, Inc., Arlington, Tex.

[21] Appl. No.: 08/767,267

[22] Filed: Dec. 13, 1996

[51] Int. Cl.[7] ................................................. B29C 43/38
[52] U.S. Cl. .......................... 264/322; 264/323; 264/327; 425/384; 425/393
[58] Field of Search ....................... 264/296, 322, 264/323, 327; 425/393, 384

[56] References Cited

U.S. PATENT DOCUMENTS

| | | | |
|---|---|---|---|
| 4,155,966 | 5/1979 | Tschanz et al. ........................ | 264/327 |
| 4,207,283 | 6/1980 | French et al. .......................... | 264/322 |
| 4,404,159 | 9/1983 | McFarlane ............................. | 264/296 |
| 4,446,084 | 5/1984 | Rowley .................................. | 264/327 |
| 4,551,292 | 11/1985 | Fletcher et al. ........................ | 264/327 |
| 4,661,300 | 4/1987 | Daughterty ............................ | 264/320 |
| 4,961,809 | 10/1990 | Martin .................................... | 264/322 |
| 5,135,599 | 8/1992 | Martin et al. .......................... | 264/322 |
| 5,306,377 | 4/1994 | Jensen et al. . | |
| 5,360,330 | 11/1994 | Jensen et al. .......................... | 264/327 |
| 5,397,512 | 3/1995 | Sloane, Jr. et al. ..................... | 264/25 |
| 5,409,644 | 4/1995 | Martin et al. .......................... | 264/296 |
| 5,425,903 | 6/1995 | Sloane, Jr. et al. ..................... | 264/22 |
| 5,484,422 | 1/1996 | Sloane, Jr. et al. ..................... | 604/272 |

FOREIGN PATENT DOCUMENTS 1 150 713   1/1958   France .

Primary Examiner—Jan H. Silbaugh
Assistant Examiner—Mark Eashoo
Attorney, Agent, or Firm—Joseph F. Shirtz

[57] ABSTRACT

A process for forming a catheter tip is described wherein a mold having an internal surface complimentary to the desired external surface of the catheter tip is formed such that it has two temperature zones. A first higher temperature zone is positioned proximally of the catheter distal tip and a lower temperature zone is positioned distal to the higher temperature zone. A catheter to be tipped is placed upon a mandrel or needle and the mold is heated. Upon insertion of the catheter and mandrel into the mold. The catheter material softens and begins to flow within the mold. The higher temperature portion supplies the heat necessary to soften the catheter material and it flow to the lower temperature zone wherein the lower temperature causes the catheter material to become more viscous or resolidify. Upon becoming more viscous, the catheter material, at the very tip, acts as a dam to prevent further flow of material thus eliminating flash from the mold end.

21 Claims, 3 Drawing Sheets

THERMAL GRADIENT BEVELING OF CATHETERS

FIELD OF THE INVENTION

The present invention relates to processes for forming conduits such as catheters with a beveled tip in order to ease insertion, and in particular, it relates to methods of forming beveled tips on peripherally inserted I.V. catheters.

BACKGROUND OF THE INVENTION

It has long been known that a beveled tip on a peripherally inserted catheter is an advantage as it eases the insertion of the catheter into the body of a patient. Intravenous catheters are used for infusing blood, plasma, drugs or other fluids into a patient's body as well as withdrawing blood or permitting the introduction of other objects such as smaller catheters through an opening in the skin. Catheters, when manufactured as original blanks, are cut from tubing stock or extruded in place. The tubing stock or extruded catheter tubing often has a blunt, abruptended tip which would cause trauma upon insertion. Therefore, many peripherally inserted catheters are beveled starting at a distance from the distal tip, a 3° taper, for example, may be used, and a terminus 27° taper over a very short portion of the varied tip is used to ease the initial insertion as a needle passes into the patient carrying the catheter tube.

Many methods for tapering a catheter tip are known in the art, for example, U.S. Pat. No. 4,661,300, entitled "Method and Apparatus for Flashless Tipping of an IV Catheter" shows a mold method wherein an end of the catheter is clipped off during the molding process. U.S. Pat. Nos. 5,397,512, 5,425,903, and 5,484,422 show a laser method of forming a beveled tip to a catheter wherein the 3° taper is initially formed on a catheter and the later 27° taper is formed via a laser contacting the catheter tube and ablating the surface in order to form the necessary taper.

SUMMARY OF THE INVENTION

The present invention relates to providing a thermal gradient within a mold for forming catheter tips. The thermal gradient is such that in a first portion of the mold a higher temperature portion is provided which causes the polymer material of the catheter tube to melt and flow. A second lower temperature portion is provided that permits the flowing polymer material to become more viscous or begin to reharden and act as a dam to prevent further flow of the polymer material in the mold.

In order to accomplish this, a mandrel or needle is used to position and support the catheter the tube to be tipped; a tipping die which is tapered in its internal configuration is heated. The tipping die has been provided with an external configuration that may provide sufficient heating to melt the catheter and also allow for rapid cooling, to permit cooling of at least a portion of the mold. This mold is mounted into a carriage that moves toward the mandrel or needle. The mandrel or needle moves through the entire die until it protrudes and the heated die acts to soften the catheter tube material and then is cooled to allow the material to fill the entire internal die space. Focused air cooling may be used in a timely fashion to rapidly cool the material creating the necessary viscosity change to allow for complete filling of the internal die shape. The external shape provides the thermal gradient to be created within the internal configuration of the mold. This allows the material to be heated for flow and to be rapidly cooled to fill the internal die space.

The tipping die can be configured with two or more materials with different thermal conductivities in an alternative fashion to provide the thermal gradient for types of plastics to stop flowing within the die. Furthermore, focused heating may provide precision placement of the heating source that will allow the entire internal configuration of the die to be filled without creating any flash.

BRIEF DESCRIPTION OF THE DRAWINGS

The invention will now be described with reference to the accompanying figures wherein.

DETAILED DESCRIPTION OF THE PREFERRED EMBODIMENT

As part of a normal catheter-forming function, a catheter preform is formed having a luer fitting in the form of a hub attached to a distally-extending tubular portion which is intended to be received within the body of a patient. This preform prior to having a necessary beveled tip provided thereon is used as incoming material to the operation of the present invention. The preform is received over a concentric pin. For example, for a 20 gauge catheter, a pin of 0.0282 inch size is inserted within the catheter tube and extends beyond the end of the catheter. The pin is preferably made of stainless steel or other metallic material that can be accurately machined to size and shape. Preferably the pin material is softer than the mold material thus reducing the damage or wear to the mold. The catheter tube 1 and pin 2 are moved concurrently with one another substantially as a unit in at least one embodiment of the present invention.

Figure 4:
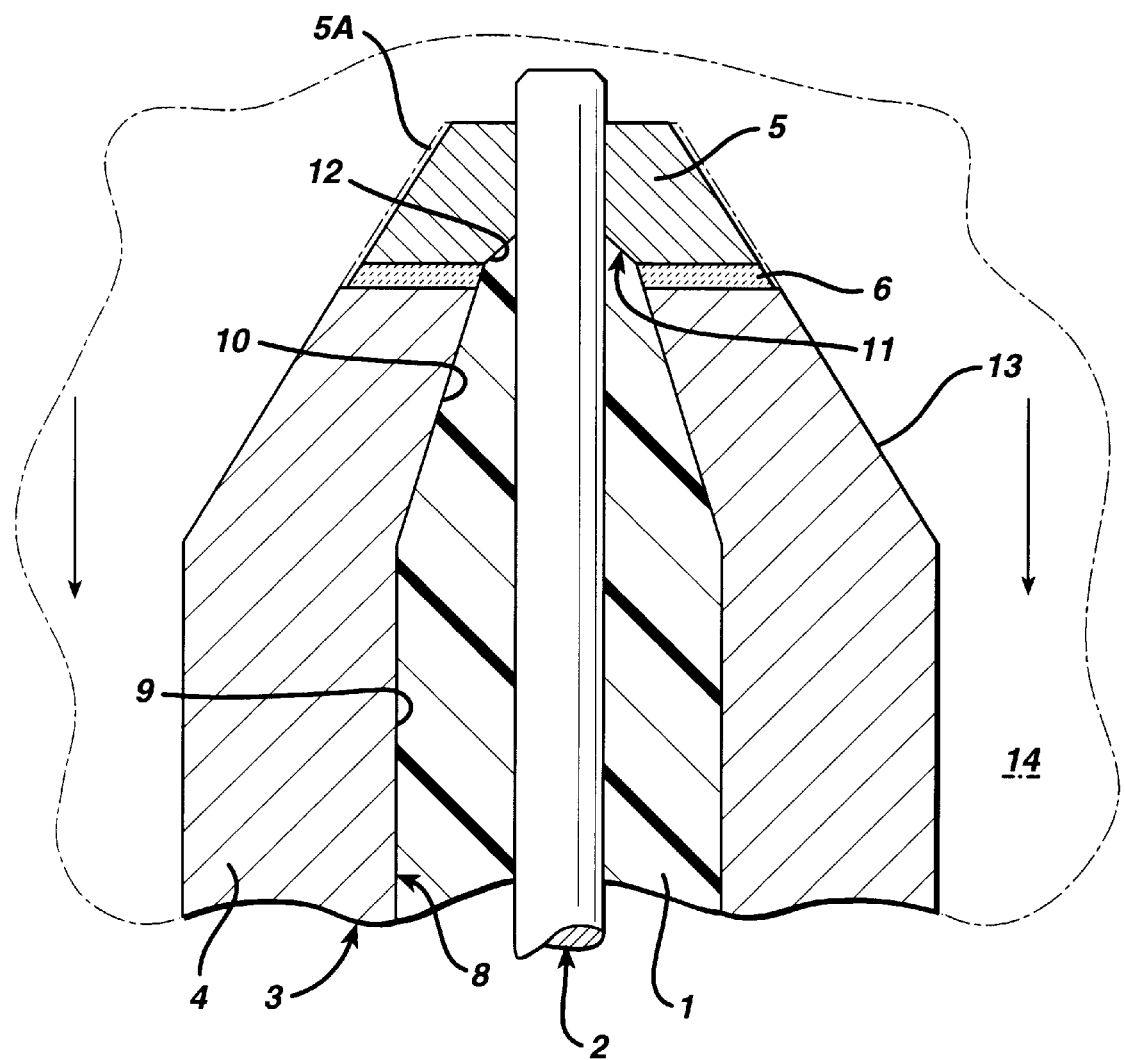
FIG. 4 is a cross-sectional view of an alternate embodiment of the invention.

A mold 3 is provided having at least two portions, a higher temperature portion 4 and a lower temperature portion 5 are separated, for example, by a ceramic insulator 6. The higher temperature portion 4 is made preferably of stainless steel or other conductive metal and is selected for its characteristics as a mold material as well as its heat conductance and retention (i.e., specific heat). The insulator 6 (FIG. 4) is preferably ceramic and is selected in order to lessen or prevent the heat transfer from the higher temperature portion 4 to the lower temperature portion 5. Lower temperature portion 5 is preferably made of ceramic (FIG. 1) or titanium alloy (FIG. 4) such as an alloy with 6% aluminum, 4% vanadium and is selected in size so as to be a smaller heat mass than the higher temperature portion 4.

The lower temperature portion 5 has an opening 7 defined therein through which the pin 2 will pass. If a pin of 0.0282 inch size is used, a 0.0285 inch diameter opening is formed to provide clearance for the pin and permit venting of air and gas as the plastic advances in the mold. Inner surface 8 of the high temperature portion has formed therein a cylindrical surface 9 and a tapered surface 10. The tapered surface 10 is formed in the shape of a cone having a 3° taper thus forming a gentle taper to the end of the catheter material upon molding. The lower temperature portion 5 may be made of ceramic thus eliminating the need for a separate ceramic insulator.

Inner surface 11 of the lower temperature portion has formed therein a frusto-conical surface 12 complimentary to a 27° tapered portion desired on the distal tip of the catheter. As can now be seen, when the pin 2 is in place within the mold 3, the outer surface of the pin 2 forms along with cylindrical surface 9, tapered surface 10, and tapered surface 12 a shape having a space forming the desired tip configuration of the catheter. That is, the inner surfaces of the mold and outer surface of the pin form surfaces complimentary to the catheter to be formed.

Figure 1:
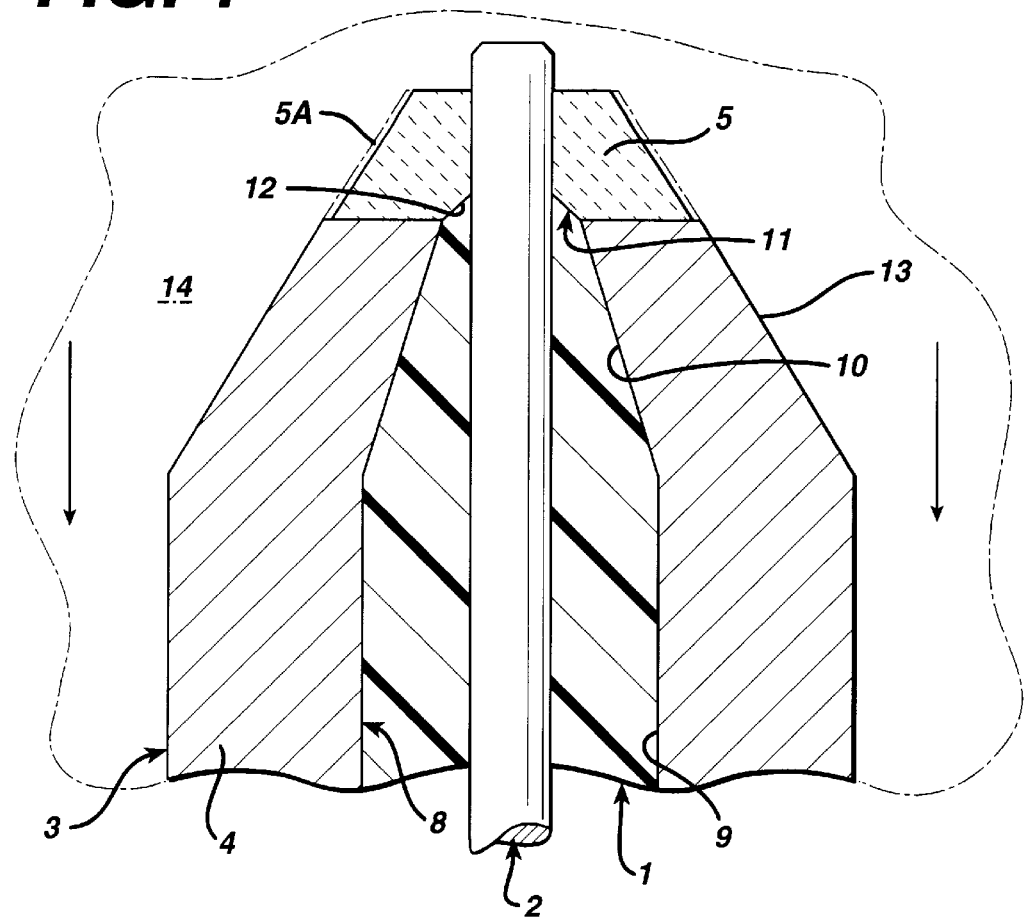
FIG. 1 is a cross-sectional view of a mold and mandrel used in a tipping operation.
Figure 2:
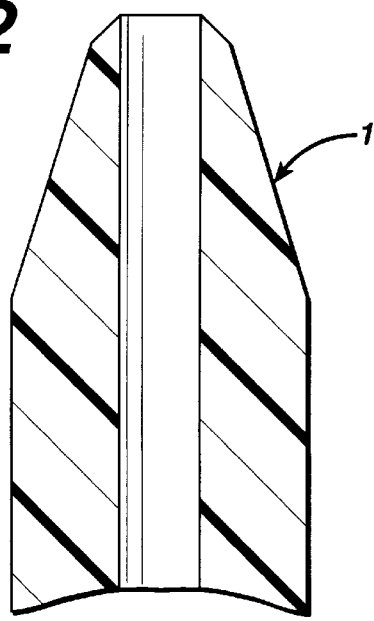
FIG. 2 is a cross-sectional view of a catheter tipped using the process of the present invention.
Figure 3:
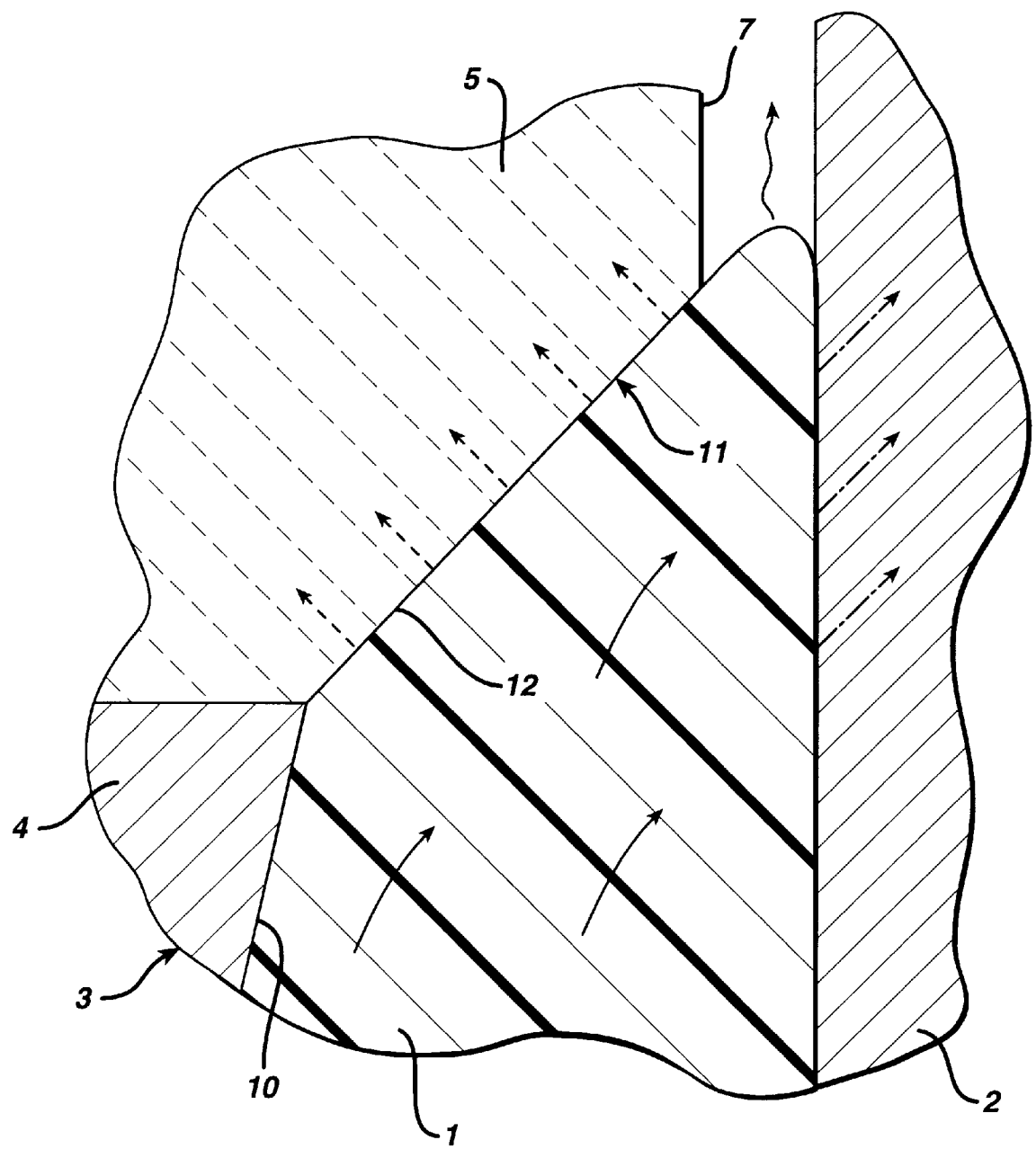
FIG. 3 is a partial cross section enlarged to show the tip area of the mold used in the process of the present invention.

The mold 3 has an outer tapered surface 13. As can be seen in FIG. 1, the outer tapered surface 13 has a slight relief portion formed adjacent to the lower temperature portion 5. A heating block 14 is provided to heat the mold. The heating block 14 is constructed as a large thermal mass in order to quickly transfer heat to the mold. The mold 3 is received within a complimentary taper within the heating block, such that the outer surface 13 contacts the heating block and therefore receives heat transfer from the heating block to the mold. The space 5A between the lower temperature portion 5 and the heating block prevents or substantially reduces the amount of heat transferred from the heating block to this portion of the mold. When the lower temperature portion is made of ceramic the space 5A is advantageous but is more advantageous in the embodiment of FIG. 4. As can easily be seen therefore, once the mold is heated to its appropriate temperature, the higher temperature portion has received a portion of the heat transferred from the heating block while the lower temperature portion has received a reduced portion or very little heat transferred from the heating block. In this way, the mold is brought up to a condition having a temperature gradient from the higher temperature portion 4 to the lower temperature portion 5. The mold and heating block are shown in contact during the molding operation in the Figures. However, in use they are separated prior to insertion of the catheter to permit cooling of the mold to resolidify the polymer. After the complete molding operation the mold is recontacted with heating block to heat it for the next molding operation.

In a preferred embodiment for a catheter of fluorinated ethylene propylene polymer material, the higher temperature portion is approximately 575°–650° F. and the lower temperature portion is approximately 100° less. Thereafter the pin 2 is inserted within the mold. In a preferred embodiment, the pin has previously received the catheter tube 1 thereon and as the pin passes through the mold and out the distal end of the mold (that is, the end adjacent the lower temperature portion) the catheter material is forced into the space defined by the pin and cylindrical surface 9, tapered surface 10 and tapered surface 12. The catheter is made of a thermoplastic material such as fluorinated ethylene propylene polymer or polyurethane. In the instance of fluorinated ethylene propylene polymer material, which has a softening temperature of 550° F., the higher temperature portion of the mold is heated to approximately 575°–650° F. Upon contacting or moving into the vicinity of this higher temperature portion, the catheter tube 1 softens and begins to flow. As used herein, flow does not necessarily mean a liquid state, but rather a pliable state of permitting easy plastic deformation of the material due to the warming and softening of the material. As the catheter is advanced into the mold space, the flowing catheter material flows along and conforms to the tapered surface 10 until it meets inner surface 11. Inner surface 11 is at a sufficiently lower temperature than inner surface 10 to permit the catheter material to begin to reharden or at least become more viscous than in the high temperature portion 4 of the mold. In this way, the material which is received along the inner surface 11 begins to act as a dam preventing the further flow of material and permits the full filling of the mold itself without excessive flash.

The pin 2 is selected such that it is slightly smaller than the opening 7 and may pass therethrough with a slight clearance. This slight clearance permits the escape of gases forward of the catheter material within the mold. However the mold material does not flash beyond the inner surface 11 as the cooler temperature causes the flowing catheter material to become more viscous and therefore less likely to flash through the small clearance provided in the mold tip.

It may easily be seen that the high temperature and low temperature portions of the mold may merely be provided by the shape of the mold rather than differing materials. For example, the low temperature portion of the mold may have fins cut therein in order to encourage the cooling of the mold in that area while the high temperature portion of the mold has a large thermal mass to provide a reservoir of heat energy thus lessening its ability to cool. In this way, the cooled area of the low temperature portion of the mold would provide the temperature gradient from the higher temperature portion surrounded by the thermal mass in order to create the damming effect of the flowing thermoplastic material.

In an alternative embodiment, the pin 2 may be permanently emplaced within the mold or passed through the mold from the distal end into the mold, such that the catheter is thereafter placed on the pin by passing a tip of the pin through the distal end of the catheter material, sliding the catheter along the pin until it engages the inner surface of the mold and further urging the catheter within the mold, such that the softened material flows from the higher temperature portion to the lower temperature portion. After formation of the final catheter product, the pin may be withdrawn through the top of the mold (the end of the mold distal from the insertion of the catheter) and the catheter thereafter or prior to withdrawal of the pin may be withdrawn from the mold.

The invention has now been described with reference to its preferred embodiments. The attached claims are directed to the invention, however, one may make many variations from those described in the preferred embodiment still in keeping with the spirit and scope of the attached claims.

What is claimed is:

1. A process for forming a beleved tip on a catheter comprising:
    a) placing a tubular catheter on a pin with the pin extending within said tubular catheter such that the pin extends beyond the tip of the catheter;
    b) heating a mold having an internal surface complimentary to a desired external beleved tip surface of the catheter, said mold, when heated, having a higher temperature zone and a lower temperature zone distal of the higher temperature zone;
    c) inserting the pin and catheter together into said mold such that the pin reaches at least a distal end of said internal surface to a form a space defined at least partially by the pin and said internal surface;
    d) continuing to advance said catheter into said space such that said higher temperature zone causes the material of said catheter to soften and flow until said material contacts said lower temperature zone, said lower temperature zone causing said material to become more viscous and act as a dam preventing further flow of said material and permitting formation of the beleved tip without exessive flash; and,
    e) removing said catheter from said mold.

2. The process according to claim 1 wherein said mold is heated by contacting an outer surface of said mold to a heater block at a temperature higher than said mold to transfer heat to said mold.

3. The process according to claim 2 wherein said mold is made of a first material in said higher temperature zone and a second material having a lower heat conductance in said lower temperature zone.

4. The process according to claim 2 wherein said mold is shaped to provide less heat transfer from said heater block to said lower temperature zone than the heat transfer to said higher temperature zone.

5. The process according to claim 4 wherein said mold contacts said heater block along said higher temperature zone and does not contact said heater block along said low temperature zone.

6. The process according to claim 2 wherein said mold is shaped to cool said lower temperature zone faster than said higher temperature zone.

7. The process according to claim 1 wherein said pin and said catheter are withdrawn from said mold.

8. The process according to claim 1 wherein the pin is removed from said mold and catheter, and thereafter said catheter is removed from said mold.

9. The process according to claim 1 wherein said mold has an insulating zone between said high temperature zone and said low temperature zone.

10. A process for forming a beveled tip on a catheter comprising:

a) heating a mold having an internal surface complimentary to a desired external tip beveled surface of the catheter, said mold having extending therefrom a pin for receiving said catheter thereupon, said mold, when heated, having a higher temperature zone and a lower temperature zone distal of the higher zone;

b) inserting said pin into a tubular catheter and advancing said catheter into said mold;

c) continuing to advance said catheter into said mold such that said higher temperature zone causes the material of said catheter to soften and flow until said material contacts said lower temperature zone, said lower temperature zone causing said material to become more viscous and act as a dam preventing further flow of said material and permitting formation of the beveled tip without excessive flash.

11. The process according to claim 10 wherein said mold is heated by contacting an outer surface of said mold to a heater block at a temperature higher than said mold to transfer heat to said mold.

12. The process according to claim 11 wherein said mold is shaped to provide less heat transfer from said heater block to said lower temperature zone than the heat transfer to said higher temperature zone.

13. The process according to claim 11 wherein said mold is shaped to cool said lower temperature zone faster than said higher temperature zone.

14. The process according to claim 11 wherein said mold contacts said heater block along said higher temperature zone and does not contact said heater block along said lower temperature zone during heating.

15. The process according to claim 10 wherein said mold is made of a first material in said higher temperature zone and a second material having a lower heat conductance in said lower temperature zone.

16. The process according to claim 10 wherein said mold is made of a first material in said higher temperature zone and a second material having a lower specific heat in said lower temperature zone.

17. The process according to claim 10 wherein said catheter is thereafter removed from said mold.

18. The process according to claim 10 wherein the pin is removed from said mold and catheter, and thereafter said catheter is removed from said mold.

19. The process according to claim 10 wherein there is an insulator provided in said mold between said high temperature zone and said low temperature zone.

20. The process according to claim 10 wherein cooling air is blown upon the mold to cool the mold and re-solidify the catheter.

21. The process according to claim 20 wherein the cooling air is focused at least in part upon the lower temperature zone.

* * * * *